United States Patent [19]
Petroff

[11] Patent Number: 5,138,165
[45] Date of Patent: Aug. 11, 1992

[54] THREE DIMENSIONAL POSITRON EMISSION TOMOGRAPHY SYSTEM

[75] Inventor: Michael D. Petroff, Fullerton, Calif.

[73] Assignee: Rockwell International Corporation, Seal Beach, Calif.

[21] Appl. No.: 785,848

[22] Filed: Oct. 31, 1991

[51] Int. Cl.$^5$ .................................. G01T 1/164
[52] U.S. Cl. ...................... 250/363; 250/363.04
[58] Field of Search .............. 250/363.03, 366, 367, 250/369, 363.04; 364/413.13, 413.24

[56] References Cited

U.S. PATENT DOCUMENTS

| | | | |
|---|---|---|---|
| 4,291,228 | 9/1981 | Thompson | 250/363 |
| 4,415,807 | 11/1983 | Friauf et al. | 250/369 |
| 4,563,582 | 1/1986 | Mullani | 250/363 |
| 4,586,068 | 4/1986 | Petroff et al. | 357/30 |
| 4,647,779 | 3/1987 | Wong | 250/363 |
| 4,677,299 | 6/1987 | Wong | 250/363 |
| 4,733,083 | 3/1988 | Wong | 250/363 |
| 4,743,764 | 5/1988 | Casey et al. | 250/363 |
| 4,864,138 | 9/1989 | Mullani | 250/363.03 |
| 4,883,966 | 11/1989 | Wong | 250/363.02 |
| 4,962,304 | 10/1990 | Stapelbroek et al. | 250/211 J |

OTHER PUBLICATIONS

Colsher, Fully three-dimensional positron emission tomography, Phys. Med. Biol., vol. 25, pp. 103-115 (1980).

*Primary Examiner*—Carolyn E. Fields
*Attorney, Agent, or Firm*—John J. Deinken

[57] ABSTRACT

A three dimensional positron emission tomography system is used in conjunction with a short lifetime positron emitter introduced into a test object to function as a tracer. A plurality of high density, high atomic number scintillating crystals are positioned within a cylindrical volume surrounding the test object, each such crystal being adapted to emit visible light in response to absorption of a gamma ray photon emitted when a positron from the tracer annihilates with an electron within the test object. A plurality of visible light photon counters is provided, with each such counter associated with one of the scintillating crystals such that the emission of visible light from the crystal is detected by the counter. Electronic circuitry sequentially polls the plurality of counters and compiles data indicative of the time at which a visible light photon was detected by each photon counter. A data analyzing system determines, from the time data and the spatial position of each crystal, the time at which and the location within the test subject from which each gamma ray photon originated.

1 Claim, 3 Drawing Sheets

THREE DIMENSIONAL POSITRON EMISSION TOMOGRAPHY SYSTEM

BACKGROUND OF THE INVENTION

This invention is concerned with positron emission tomography systems.

Positron emission tomography (PET) is a type of nuclear imaging which is used in a variety of applications, particularly in medical research and diagnostic techniques. In a typical PET system, a radioactive compound, such as a fluorodeoxyglucose (a radiopharmaceutical), is administered to the patient being tested. The isotope is used to label a substance which circulates with the blood and which may be absorbed in certain tissues.

The isotopes used in PET systems decay be emitting a positively charged particle with the same mass as the electron (a positron) and the neutrino from the nucleus. In this process one of the protons in the nucleus becomes a neutron, so that its atomic number declines while its atomic weight remains constant. The positron is ejected with a kinetic energy of up to 2 MeV, depending on the isotope, and loses this energy by collisions as it travels within the body of the patient. When the positron reaches a thermal energy level, it interacts with an electron, resulting in mutual annihilation of the two particles. The rest mass of the two particles is transformed into two gamma rays of 511 KeV, which are characteristically emitted at 180° with respect to each other.

The two gamma rays may be detected by suitable devices. These devices are normally scintillation detectors arranged in a precise geometrical pattern around the patient. A scintillation detector emits a light flash, with the intensity of the light proportional to the energy of the gamma ray, each time it absorbs gamma radiation, although this gamma radiation may or may not have arisen from the mutual annihilation of the positron and the electron.

Typically, a photomultiplier is used to convert the light flashes from the scintillation detector into an electrical charge pulse whose amplitude is proportional to the intensity of the light. If two detectors measure the energy of the gamma rays at about 511 KeV (i.e., equivalent to the mass of an electron at rest) and register this event almost simultaneously, it may be assumed that the origin of the radiation is on a straight line between the two detectors. Sufficient detectors are used in an arrangement designed to ensure that many coincident events may be imaged during the same time interval. The information from these detectors may then be processed by a computer using image reconstruction techniques in order to map the locations of the positron emitting isotope within the patient.

In prior art designs, PET imaging of a three dimensional object is typically obtained by using multiple rings of detectors, with each ring providing information from which a portion of the image corresponding to a "slice" through the patient can be developed. Three dimensional PET imaging would be preferable, but direct three dimensional PET imagers have so far been considered only theoretically because of the difficulty of obtaining sufficient readout of light from small, densely packed scintillation crystals by photomultiplier tubes.

SUMMARY OF THE INVENTION

A three dimensional positron emission tomography system is used in conjunction with a short lifetime positron emitter introduced into a test object to function as a tracer. The system lifetime a plurality of high density, high atomic number scintillating crystals, the crystals being positioned within a cylindrical volume surrounding the test object, each such crystals being adapted to emit visible light in response to absorption of a gamma ray photon emitted when a positron from the tracer annihilates with an electron within the test object. A plurality of visible light photon counters is provided, with each such counter associated with one of the scintillating crystals such that the emission of visible light from the crystal is detected by the counter. Electronic circuitry sequentially polls the plurality of counters and compiles data indicative of the time at which a visible light photon was detected by each photon counter. A data analyzing system determines, from the time data and the spatial position of each crystal, the time at which the location within the test subject from which each gamma ray photon originated.

DESCRIPTION OF THE INVENTION

Figure 1:
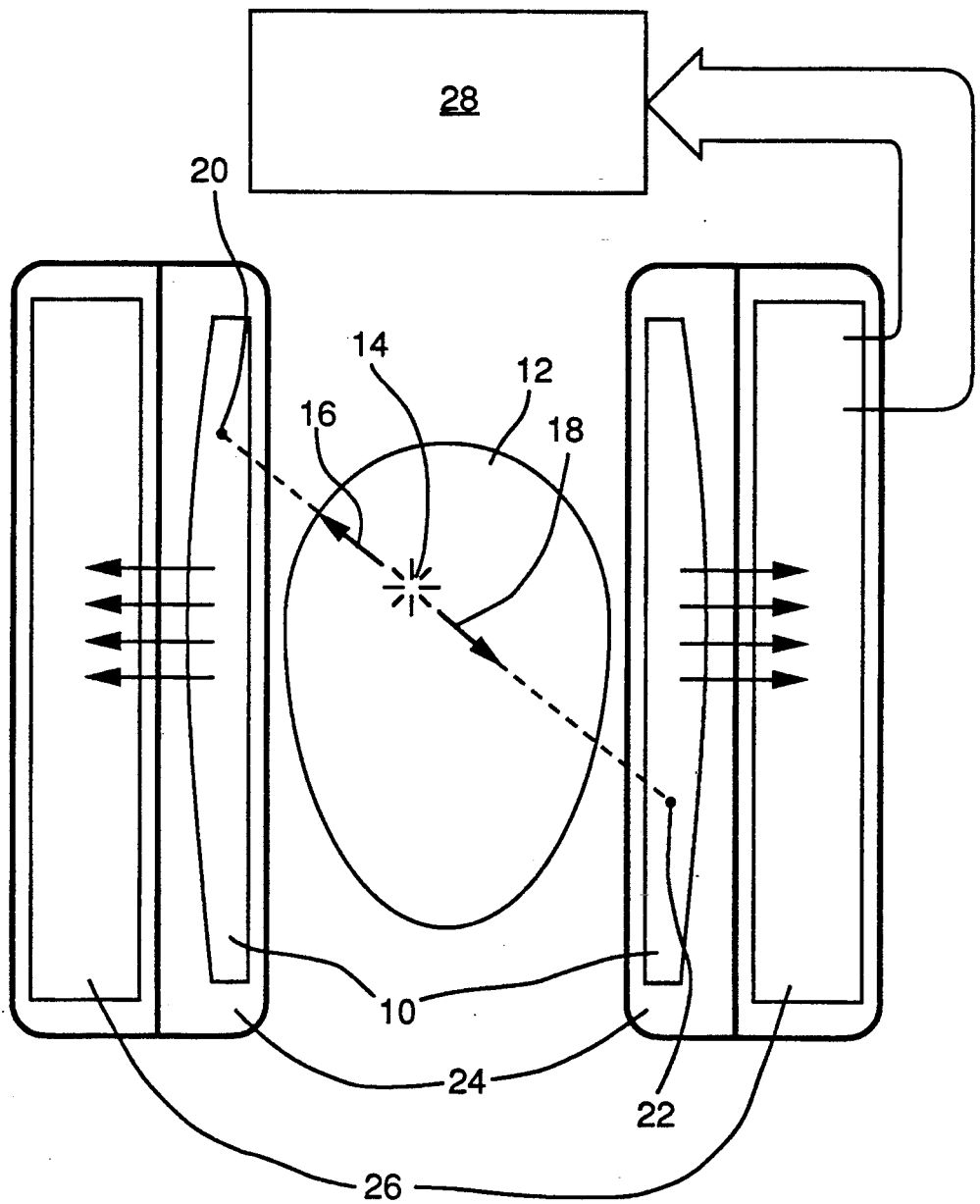
FIG. 1 is a vertical cross-sectional view of a three dimensional positron emission tomography system.

FIG. 1 is a vertical cross-sectional view of a three dimensional positron emission tomography system constructed according to the present invention. In this embodiment, an array of high density, high atomic number scintillating crystals, such as BGO ($Bi_4Ge_3O_{12}$) is positioned within a cylindrical volume 10 which surrounds the head 12 of a patient being tested. In the embodiment illustrated, the array includes approximately 200,000 BGO crystals having dimensions of 3 mm×3 mm×5 mm. A short lifetime positron emitter is introduced into the patient to function as a tracer. The positron tracer attaches to molecules such as glucose which are distributed by blood vessels to active regions of the brain.

When a positron from the tracer is emitted within the patient, as at point 14, the positron will annihilate with an electron, resulting in the emission of two 511 KeV gamma ray photons 16 and 18 in opposite directions. When the gamma ray photons are each absorbed by a crystal in the array, as by the crystals positioned at locations 20 and 22, each crystal emits visible light. A visible light photon counter is positioned adjacent to each crystal in the array, so that the emission of visible light from each crystal is detected by the associated counter (the crystals and counters are contained within a liquid helium cryostat 24 to ensure that the counters ar cooled to the low temperature required for their proper operation). Electronic circuitry, as indicated by the block 26, is connected to the array of counters. In conjunction with a computer 28, the electronic circuitry monitors the array of counters so that data is compiled to indicate the times at which visible light photons are detected at the location of each counter in the array. Using this data, the computer can determine each incidence of coincident detection of two 511 KeV gamma ray photons. From this data, computer tomography can produce an image which provides information about the condition of the patient, such as brain activity. Since the operation of such electronic circuitry and of such a computer are well known to those skilled in the pertinent art, further details regarding these portions of the PET system are not necessary to the description of this invention. Further information regarding the structure and operation of visible light photon counters may be obtained by referring to Petroff, et al., Solid State Photomultiplier, U.S. Pat. No. 4,586,068, and Stapelbroek, et al., Intrinsic Impurity Band Conduction Detectors, U.S. Pat. No. 4,962,304.

Figure 2:
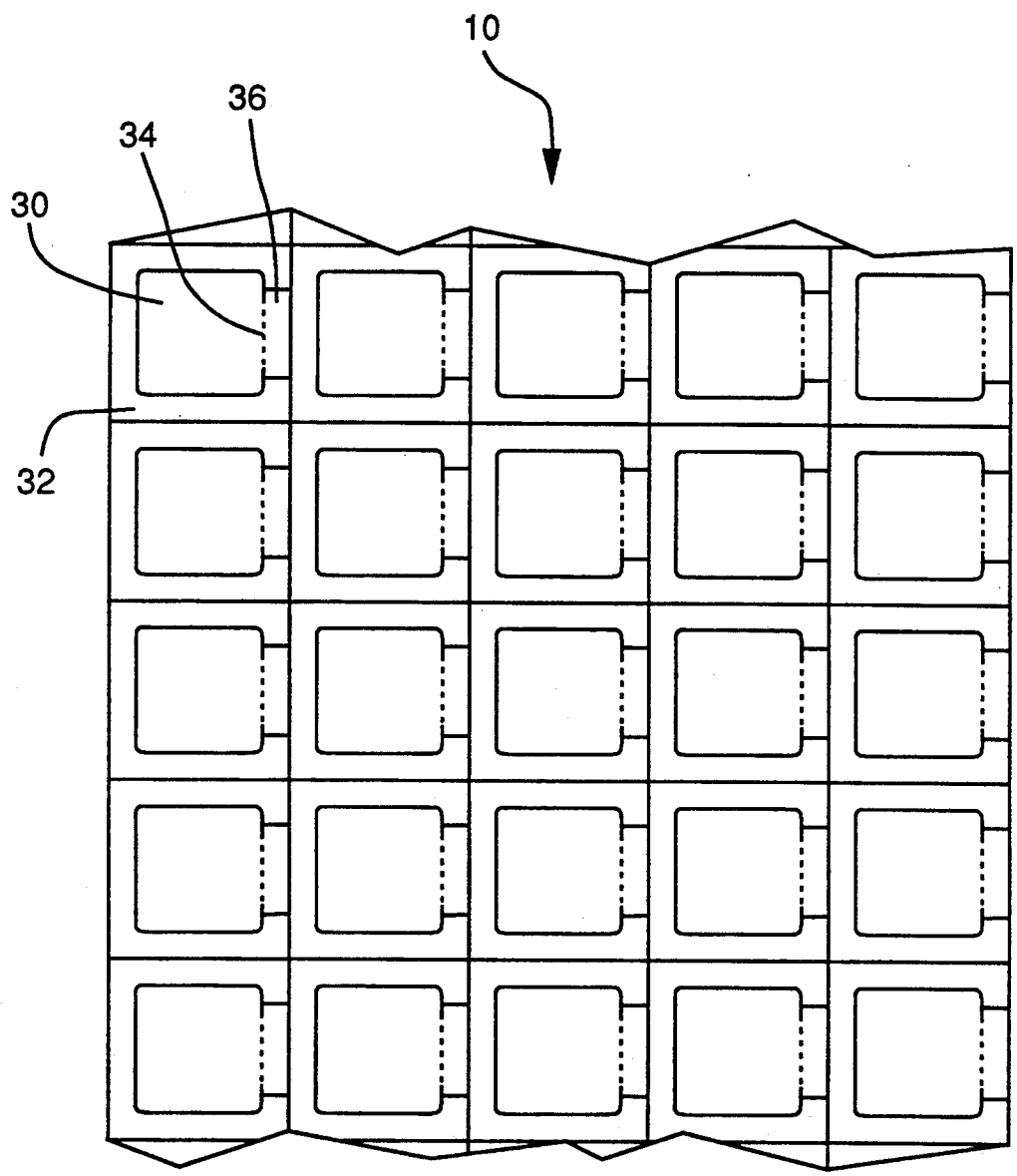
FIG. 2 is a vertical cross-sectional view of a portion of FIG. 1.
Figure 3:
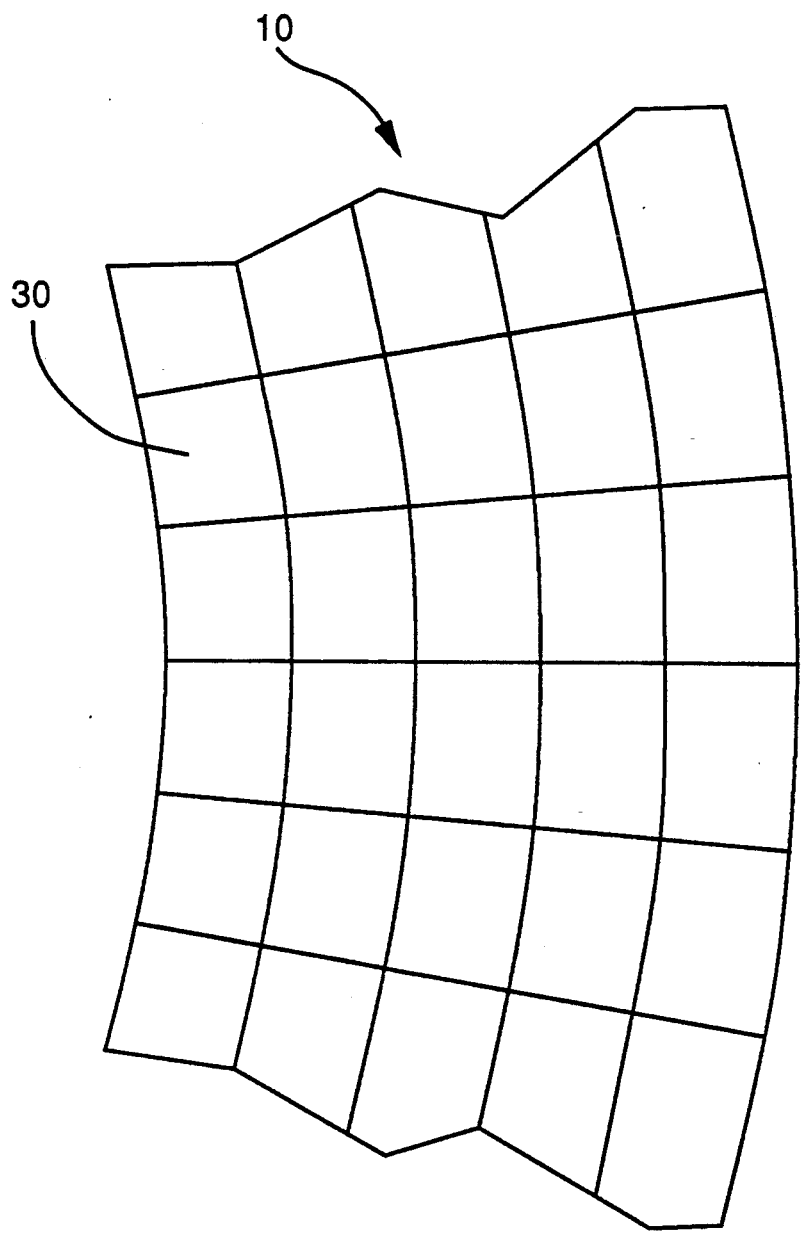
FIG. 3 is a horizontal cross-sectional view of a similar portion.

FIG. 2 is an enlarged vertical cross-sectional view of a portion of FIG. 1, while FIG. 3 is a horizontal cross-sectional view of a similar portion. These figures are shown in a larger scale than FIG. 1 in order to illustrate the positional relationship between the scintillation crystals and the visible light photon counters which is achieved in this invention. Each approximately $3 \times 3 \times 5$ mm$^3$ BGO crystal, such as the crystal 30, is coated with a layer 32 of MgO, except for a $1 \times 1$ mm$^2$ opening, such as the opening 34, with the opening facing a $1.2 \times 1.2$ mm$^2$ visible light photon counter, such as the counter 36. With the arrangement of FIGS. 2 and 3, approximately 90% of the incident 0.51 MeV photons will be detected in a 2.5 cm thickness of GBO. When absorption in tissue and bone as well as losses into angles not intercepted by the detectors are taken into account, about 7% of the positron decays in the brain region of the patient's head will be detected as coincidences of 511 KeV photons.

Data obtained using an arrangement of small BGO crystals at a temperature of 7 K indicated that as many as $2 \times 10^3$ photons are detectable by a $1.0 \times 1.8$ mm$^2$ area visible light photon counter when a 511 KeV gamma photon is totally absorbed by BGO. The decay time at 7 K has been measured to be about 150 $\mu$s. Detection of a scintillation with a high probability (95%, for example) will require detecting one photon out of three photons in the leading edge of the decaying train of scintillation photon pulses. This is based on the probability of zero counts being 5% when the average is three counts in a randomly occurring sequence of counts. If a 511 KeV photon is totally absorbed, the average time for emission of three scintillation photons is about 0.23 $\mu$s. Thus, although the GBO scintillation decay time at 7 K is long (150 $\mu$s), the first photons of a scintillation are detected in less than 0.3 $\mu$s with a 95% probability. Evaluation of 95% of the light yield (proportional to the gamma energy) is accomplished in less than 0.5 ms by counting photons for a period of several scintillation decay times.

Each crystal-counter unit detecting a scintillation is configured to send to the computer a digital signal (18 bit address) indicating the positional coordinates of the crystal within the array, the onset time of the scintillations, and the number of photons which were detected. The computer will sort out the coincidence events in which the total number of scintillation photons in a BGO crystal and its near neighbors add to the total number expected for a 0.51 MeV positron annihilation gamma ray. For this scheme to function properly, the number of all BGO scintillation events per second must be kept below a level where accidental coincidences become too frequent. If 0.3 $\mu$s is the coincident time gate then the number of events of all types should be less than about $3 \times 10^4$ per second for all 200,000 of the crystals, to avoid exceeding a 1% accidental rate. With the measured BGO scintillation decay time of 150 $\mu$s at 7 K the data acquisition rate needed to form an image may be relatively slow, about $3 \times 10^3$ projection events per second. Typically about $10^7$ projection events are needed for a complete PET brain scan, so that a complete scan should take about one hour. The radiation dose for a three dimensional PET system constructed according to this invention will, however, be very small compared to that of two dimensional PET systems (which may be as much as 100 times higher). Moreover, the performance of the proposed three dimensional PET system can be greatly improved if the scintillation decay time of BGO or other possible crystals can be made much less than 150 $\mu$s without substantial loss in light yield. This may be possible with appropriate dopants in the crystals that provide alternate decay modes through levels of intermediate energy. Since the light emitted may be of lower energy than that of pure BGO, the longer wavelength capability of visible light photon counters should prove to be very useful.

The preferred embodiments of this invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

The teaching of the following documents, which are referred to herein, is incorporated by reference:

Petroff, et al., Solid State Photomultiplier, U.S. Pat. No. 4,586,068;

Stapelbroek, et al., Intrinsic Impurity Band Conduction Detectors, U.S. Pat. No. 4,962,304.

I claim:

1. A three dimensional positron emission tomography system, for use in conjunction with a short lifetime positron emitter introduced into a test object to function as a tracer, comprising:

a plurality of high density, high atomic number scintillating crystals, the crystals being positioned with a cylindrical volume surrounding the test object, each such crystal being adapted to emit visible light in response to absorption of a gamma ray photon emitted when a positron from the tracer annihilates with an electron within the test object;

a plurality of visible light photon counters, each such counter associated with one of the scintillating crystals such that the emission of visible light from the crystal is detected by the counter;

circuitry for sequentially polling the plurality of counters to compile data indicative of the time at which a visible light photon is detected by each photon counter; and a data analyzing system for determining, from the time data and the spatial position of each crystal, the time at which the location within the test object from which each gamma ray photon originated.

* * * * *